ber: 6,156,334

United States Patent
Meyer-Ingold et al.

[11] Patent Number: 6,156,334
[45] Date of Patent: Dec. 5, 2000

[54] WOUND COVERINGS FOR REMOVAL OF INTERFERING FACTORS FROM WOUND FLUID

[75] Inventors: Wolfgang Meyer-Ingold, Hamburg; Wolfram Eichner, Butzbach; Norbert Ettner, Neu Wulmstorf; Michael Schink, Hamburg, all of Germany

[73] Assignee: Beiersdorf, AG, Hamburg, Germany

[21] Appl. No.: 09/276,687

[22] Filed: Mar. 26, 1999

[30] Foreign Application Priority Data

Mar. 27, 1998 [DE] Germany ............................ 198 13 663

[51] Int. Cl.[7] .............................. A61F 13/00; A61K 9/14; A61K 47/30; A01N 25/00
[52] U.S. Cl. ........................... 424/443; 424/443; 424/449; 424/486; 514/781; 514/772.4; 514/772.6; 514/777
[58] Field of Search .................................. 424/443, 449, 424/486; 514/777, 781, 772.4, 772.6

[56] References Cited

U.S. PATENT DOCUMENTS

| 4,122,158 | 10/1978 | Schmitt | 424/27 |
|---|---|---|---|
| 4,226,232 | 10/1980 | Spence | 128/156 |
| 5,409,703 | 4/1995 | McAnalley et al. | 424/435 |
| 6,013,106 | 1/2000 | Tweden et al. | 623/66 |

FOREIGN PATENT DOCUMENTS

| 0 075 791 | 4/1983 | European Pat. Off. . |
| 0 236 610 | 9/1987 | European Pat. Off. . |
| 29 23 802 | 12/1979 | Germany . |
| 34 357 18 | 4/1985 | Germany . |
| 34 44746 | 6/1985 | Germany . |
| 36 06 265 | 9/1987 | Germany . |
| 40 26 153 | 2/1992 | Germany . |
| 196 31 421 | 2/1998 | Germany . |
| 684783 | 12/1994 | Switzerland . |
| WO 84/01108 | 3/1984 | WIPO ............................ A61L 15/03 |

*Primary Examiner*—Thurman K. Page
*Assistant Examiner*—Isio Ghali
*Attorney, Agent, or Firm*—Nixon & Vanderhye PC

[57] ABSTRACT

The invention relates to novel wound coverings with which interfering factors of the wound healing process can be removed from the wound fluid of chronic wounds in a controlled manner and the normal healing process is promoted.

7 Claims, 4 Drawing Sheets

BONDING OF PDGF-AB BY ANTI-PDGF ANTIBODIES IMMOBILIZED ON CELLULOSE

WOUND COVERINGS FOR REMOVAL OF INTERFERING FACTORS FROM WOUND FLUID

The invention relates novel wound coverings with which it is possible to remove interfering factors of the wound healing process from the wound fluid of chronic wounds in a targeted manner and in this way to initiate or promote the normal healing process.

The treatment of wounds which heal poorly or not at all has always been a problem which it has not hitherto been possible to solve satisfactorily. In the past, attempts have been made to promote wound healing by application of the most diverse substances and substance mixtures. The range of topical applications has extended from blood, serum or excrement via sulphur, pitch or heavy metal salts to milk, sugar or honey. Active compounds currently being developed for topical wound treatment are often substances endogenous to the body which are prepared by genetic engineering and are assumed to be present in the chronic wound in only a reduced amount, if at all. In some cases, it has been possible in all instances to detect a reduced concentration compared with healthy tissue. The proliferation-stimulating growth factors are an example (W. Meyer-Ingold, TIBTECH 1993, 11:387). The reasoning behind these modern set-ups is the concept that the absence or inadequate presence of such stimuli can be compensated by supplementing them and a normal wound healing which proceeds unimpeded therefore results. A large number of animal studies in recent years confirm this assumption. In spite of intensive efforts, the clinical breakthrough—apart from one exception (PDGF)—nevertheless has not yet been achieved. Even active compounds such as peptides or sugar polymers, which are derived from the natural structures of connective tissue and showed promising results in animal studies, have so far largely failed to achieve clinical success.

The disappointing results from clinical studies prompted an intensive work-wide analysis of the target of topical wound therapeutics, the chronic wound itself. Attention is mainly focused here on the exudate from the chronic wound, which is called wound fluid. Although these studies are still in their infancy, they nevertheless already show differences between chronic and acute, i.e. "normal" wound fluid, especially the observation, supported by determination of inflammatory markers (such as e.g. interleukin-1-alpha and collagenase (E. J. Barone et al., Wound Rep. Reg. 1995; 3:374), that the inflammatory character of chronic wound fluid is increased significantly compared with acute wound fluid, and furthermore is also persistent.

The current requirements of the function of wound coverings for chronic wounds are attributed to G. Winter (Nature 1962; 193:293) and have recently been reformulated by T. D. Turner (Wound Rep. Reg. 1994; 2:202). The main task is to provide a damp wound healing medium which, in contrast to traditional dry wound treatment with e.g. gauze compresses, offer physiological and therefore better conditions to the natural processes of wound healing. The wound covering here must absorb most of the exudate, but at the same time leave a film of fluid on the wound itself, in which fluid the actual moist would healing takes place. These requirements are achieved by gel- or sponge-like structure and/or additional swellable or water-binding substances in the wound covering. On the outside, a breathable film ensures permeability to oxygen and water vapour and at the same time a barrier function against germs possibly penetrating from the environment.

In this connection, it is remarkable that by varying the properties of the wound coverings in respect of absorption of liquid or permeability to water vapour, in some cases opposite effects can be observed, e.g. a general concentration of protein (cf. e.g. V. Achterberg, J. Wound Care, 1996; 5:79). The selective properties of Sorbact®, a cellulose wound covering rendered hydrophobic by coupling with stearic acid (T. Wadstrom et al., Acta Pathol. Microbiol. Immunol. Scand. 1985; 93B:359), are indeed in principle suitable for preferentially binding bacteria via hydrophobic interactions, as described in EP 0 162 026 and a clinical study by G. Friman (Current Therapeutic Research 1987; 42: 88), but a differentiation between different strains of bacteria is not possible with this.

Disadvantages of the wound coverings known in the prior art are, inter alia, the inadequate healing-promoting action on chronic wounds and the abovementioned, in some cases opposite effects which are achieved by different properties in respect of liquid absorption of permeability to water vapour of the wound coverings.

The object of the invention is therefore to provide wound coverings which are particularly suitable for initiating or promoting healing of chronic wounds, i.e. wounds which heal poorly or not at all.

The object is achieved according to the invention in that additional substances which interact with interfering factors present in wounds exudate, i.e. with factors which impede the wound healing process, are used in the production of the wound coverings, these additional substances being covalently bonded to a carrier material.

In this connection, the term "interfering factors" is understood generally as materials or substances which impede or slow down the healing process of wounds and therefore lead to the development of chronic wounds. These include suspended cells (e.g. inflammatory cells, such as leukocytes and macrophages or bacteria) and cell fragments or dissolved constituents, such as antigens, free radicals (such as e.g. reactive oxygen species, ROS), ions, (such as e.g. iron ions), proteins, peptides, lipids and free fatty acids, present in the wound exudate.

The substances which interact with these interfering factors are substances which remove the interfering factors from the wound exudate. In the following, the substances which interact with the interfering factors are also called "trapper molecules", but this name is not understood as a limitation. The removal or elimination can take place in various ways, depending on the nature of the interfering factor, i.e. by a physical, chemical or immunological route, such as, for example, by binding, complexing or chelating. In an individual case, however, the interfering factor can also be eliminated by reacting chemically with the substance (the "trapper molecule") and being converted into a compound which no longer impedes wound healing or impedes it to only a reduces extent. In the context of the present invention, the "trapper molecules" can be chosen, for example, from the group consisting of antibodies, chelators, enzyme inhibitors, enzymes, enzyme mimics, peptides and other proteins. In each case, it is particularly advantageous if the substance bonded to the carrier has a high specificity for the interfering factor to be eliminated or to be removed from the wound fluid, since removal also of substances which are important for the wound healing process and the result of an adverse effect can be prevented in this manner.

The invention accordingly relates to a wound covering, which is characterized in that substances which interact with interfering factors present in the wound exudate which impede the wound healing process are covalently bonded to a carrier material.

The advantage of the invention lies in the fact that a selective removal of the interfering factors is possible by the substances covalently bonded to the carrier material, the "trapper molecules" also being removed on removal of the wound covering, without remaining in the wound or in the wound fluid. In this manner, on the one hand introduction of further substances which, where appropriate, could impede the wound healing process into the wound with the "trapper molecules" is prevented. On the other hand, for example in the case of substances which chelate or bond in the form of a complex or in another manner the interfering factors, such as e.g. ions, enzymes or other proteins, as it were "withdraw" the interfering factors from the wound exudate on removal of the wound covering. According to the invention, the interaction can also include a conversion of interfering factors in to substances which no longer impede wound healing. The substances used for the interaction which are covalently bonded to the wound covering are thus introduced into the wound only temporarily and, after they have performed their task as intended (i.e. have undergone the abovementioned interaction), are removed from the wound region again. According to a preferred embodiment of the invention, the complexed interfering factors or such bonded to the tapper molecules are removed here at the same time. The healing process of chronic wounds, i.e. wounds which heal poorly or not at all, is improved or initiated by this selective removal or elimination of the interfering factors.

In the context of the present invention, it is therefore not only possible to generate a moist wound medium or to apply growth-promoting substances in order to improve the healing process of chronic wounds, according to the invention the healing process can be accelerated and promoted further in that interfering factors present in the wound fluid are removed or eliminated specifically, e.g. by selective bonding to a wound covering or by the abovementioned conversion processes.

In the inflammatory phase of wound healing, which follows blood clotting and blood platelet aggregation after injury and trauma, neutrophiles and monocytes preferentially migrate into the damaged tissue. They start the phagocytosis of germs and the breakdown of destroyed tissue and foreign antigene there. Activated by chemical messenger substances and microorganisms, a greatly increases production of ROS, also called "oxidative burst", occurs. These ROS are stored in granula and, on further stimulation, are released into the extracellular tissue in high local concentrations for combating microorganisms.

Another weapon of neutrophiles for combating substances foreign to the body are proteolytic enzymes, such as elastase, cathepsin G (J. Travies, American Journal of Med., 1988; 84:37) and collagenases, in particular MMP-8(M. Weckroth et al., J. Invest. Dermatol., 1996; 106:1119). They are usually stored in cytoplasmic granula and enter the extracellular medium only in a controlled manner. Rapid dissolution and sudden leakage of the cell membrane and therefore uncontrolled secretion of the proteolytic enzymes occurs by spontaneous cell death (necrosis) of the neutrophiles (C. Haslett and P. Henson, in: The Molecular and Cellular Biology of Wound Repair, 1996; Ed. R. Clark, Plenum Press, New York & London, p. 143). The secretion takes place in the form of latent proenzymes, and, after the N-terminal propeptides have been split off, leads to breakdown of the connective tissue. proteins elastin, collagen, proteoglycan (J. Travies, American Journal of Med., 1988; 84:37), fibronectin (F. Grinell and M. Zhu, J. Invest. Dermatol. 1996; 106:335; S. Herrick et al., Laboratory Investigations 1997; 77:281) and also plasma factors, such as fibrin and antithrombin III (W. Bode et al., EMBO J 1986; 5:2453), and therefore damage to the tissue and a delay in wound healing. ROS and plasmin as mediators of inflammatory cells can activate the pro-matrix metalloproteinases (pro-MMPs) (A. Docherty et al., TIBTECH 1992; 10:200) and contribute here to a further increase in the protease concentration.

In wound healing which progresses normally, after successful elimination of the triggering stimuli the inflammatory phase ends and the reconstruction of the tissue can start. However, if these stimuli persist, further leukocytes subsequently migrate into the tissue and are activated again, which leads to a permanently inflamed or chronic wound. The associated increased secretion of ROS (O. Senel et al., Annals of Plastic Surgery 1997; 39:516) and proteolytic enzymes can lead to a release of iron from damaged tissue, the plasma proteins tranferrin and ferritin (C. Thomas et al., J. Mol. Biol. 1985; 260:3275; P. Biemond et al., Free Radic. Biol. Med. 1988; 4:185), iron-containing enzymes, such as aconitase (P. R. Gardner et al., J. Mol. Biol. 1995; 270:13399) and other iron-sulphur proteins (J. Fridovich, Annu. Rev. Biochem. 1995; 64:97). The breakdown of ferritin and transferrin into the acid autophagocytic vacuoles of macrophages by lysosomal hydrolases leads to a further increase in the concentration of non-bonded iron (S. Sakaida et al., Mol. Pharmacol. 1990; 37:435). This transient, extracellular pool of released iron reacts with oxygen dissolved i the wound exudate to give iron(III) ions and superoxide, which dismutates rapidly into hydrogen peroxide. This noncharged molecule can penetrate through biological membrances, in contract to superoxide, and react further at specific points in the cytosol. It dissociates into highly reactive hydroxyl radicals, under catalysis by iron(II) ions, in the reaction called the Fenton reaction. In the presence of physiological reducing agents cyclic redox reactions occur, ROS being generated continuously (B. Halliwell and J. Gutteridge, Free Radicals in Biology and Medicine 1989; 2nd edition, Clarendon Press, Oxford). Under non-pathological conditions, iron metabolism is under strict control, and iron-medicated free radical reactions of the cell occur to only a limited extent.

The important role of iron ions and also copper ions in a cyclic redox reaction to form ROS (superoxide anions, peroxide dianions, singlet oxygen and hydroxyl radicals) and therefore the oxidative damage to biomolecules and cells has been adequately documented. Free, mobile iron and weakly complexed iron bonded to phosphoric acid esters, organic acids and membrane lipids (J. Mutantë et al., Agents Actions 1991; 32:167; D. A. Rowley et al., Clin. Sci. 1984; 66:691; B. Halliwell et al., FEBS Lett 1988; 66:691) cause e.g. damage to lysosomal membranes by lipid peroxidation with accompanying secretion of hydrolytic enzymes, DNA and RNA modification and strand breakages, degradation of polysaccharides, oxidation of amino acids and cleavage of enzymes and other protein. Reactive oxygen species are therefore held responsible for many further processes in the body, such as ageing, rheumatoid arthritis, arteriosclerosis, muscular dystrophy, Parkinson's disease or autoimmune reaction, in addition to tissue damage. Studies on leg ulcers in which an increased iron content and a reduced amount of the endogenous growth factor transforming growth factor β (TGF-β) have been found also indicate the relationship between iron ions, ROS and tissue damage. Macrophages showed the greatest iron-specific staining here, followed by fibroblasts (Y. J. Francillon et al., Wound Rep. and Regeneration 1996; 4:420). By phagocytosis of senescent erythrocytes and iron-containing proteins, the iron is deposited in intracellular depots in the form of the iron storage proteins ferritin and haemosiderin.

Since wound healing is an extremely complex biological process, within which many individual steps pass through a coordinated cascade, the possibilities of interference are also manifold. Cellular interfering factors, such as bacteria or an excess of endogenous inflammatory cells, such as leukocytes or macrophages, can slow down wound healing just as much as imbalanced regulatory proteins or peptides of the cytokine type, such as catabolic enzymes from the classes of proteases, lipases, phospholipases or glycosidases, and such as enzymes which are active in signal transduction, such as for example, kinases. Small molecules or ions are also changed in their concentration in chronic wound fluid, for example reactive oxygen species or iron ions are increased. It is therefore obvious that the removal of such interfering factors helps the normal wound healing process.

Substances which interact with interfering factors of the type mentioned e.g. to form stable complexes can also be manifold, according to the diversity of the potential interfering factors. In the context of the present invention, the "trapper molecules" are preferably proteins or organic molecules. According to a particular embodiment of the invention, specific antibodies against a cytokine, against and enzyme or against a regulatory peptide are suitable as the "trapper molecule". Antibodies are therefore primarily suitable for the removal of the abovementioned inflammatory markets, which as a rule are proteins. For as quantitative as possible a removal, for example of a defined cytokine, antibodies of high affinity (if possible greater than $10^8$ $mol^{-1}$; E. Harlow and D. Lane: Antibodies—A Laboratory Manual, 1988; p. 514, Cold Spring Harbor Laboratory) must be chosen, since otherwise complete bonding of the interfering factor cannot take place, in spite of the use of high antibody concentrations.

Further interacting substances which are to be used according to the invention are integrins (R. O. Hynes, Cell 1992; 69:11) or generally RGD peptides (i.e. peptides which contain the tripeptide sequence arginine-glycine-aspartate), which are can used in an immobilized form as specific receptors for cell-cell and cell-matrix interactions in order to bind a certain cell population in a controller manner.

Analogously, adhesins can be employed for specific bonding of bacterial surface structures (C. Heilmann et al., Mol. Microbiology 1996; 20:1083) and therefore for specific bonding of bacteria (J. M. Higashi et al., J. Biomed. Master. Res. 1998; 39:341).

Furthermore, it is possible to use inhibitors for enzymes if the formation of the corresponding enzyme-inhibitor complex proceeds irreversibly (so-called "dead-end complex"). Inhibitors which are particularly suitable according to the invention are synthetic low molecular weight inhibitors for proteolytic enzymes, such as e.g. antipain, leupeptin, cystain, pepstatin, diisopropyl fluorophosphate, 4-(2-aminoethyl)-phenylsulphonyl fluoride or phenylmethanesulphonyl fluoride. Naturally occurring, proteinogenic protease inhibitors, such as e.g. those of the class of tissue inhibitors of matrix metalloproteinases or aprotinin, anti-2-antiplasmin, alpha-2-macroglobulin, alpha-1-antichymotrypsin, soya bean trypsin inhibitor and/or alpha-1-protease inhibitor, are also suitable.

In the context of the present invention, enzymes or enzyme mimics can also be employed as the binding principle as substances which interact with the interfering factors if a corresponding substrate is the interfering factor and can be rendered harmless by reaction with the enzyme covalently bonded to the carrier. This can take place, for example, in the case of ROS.

The use of other known biological binding phenomenon, such as, for example, the property of the blood protein albumin to add on to free fatty acids, can lead to a reduction in the content of free fatty acids in wound fluid if required.

Specific chelators, such as e.g. diethylenetriaminepentaacetic acid, N,N'-bis-(o-hydroxybenzyl)-ethylenediamine-N,N'-diacetic acid, 1,2-dimethyl-3-hydroxypyrid-4-on, 1,2-dimethyl-3-hydroxy-3-hydroxypyridin-4-on (B. Porter, Acta Haematol. 1996; 95:13) and deferrioxamine (deferoxamine, 30-amino-3, 14, 25-trihydroxy-3, 9, 14, 20, 25-pentaazatriacontane-2, 10, 13, 21, 24-pentaone, DFO) (G. J. Kontoghiorghes, Toxicol. Lett. 1995; 80:1; J. B. Galey et al., Free Radic. Res. 1995; 22:67), which form complexes with very high bonding constants, are suitable foe selective removal of interfering ions such as e.g. iron ions. DFO, a bacterial siderophor isolated from *Streptomyces pilosus* (H. Bickel et al., Helv. Chim. Acta 1963; 46:1385), and its mesylate (Desferal®; DFOM) are complexing agents with a high bonding affinity in a molar ratio of 1:1 for aluminium and iron ions. DFO is built up from one molecule of acetic acid, two molecules of succinic acid and three molecules of 1-amino-5-hydroxylaminopentane, which form with iron (III) ions, via their hydroxamic acid groups, an intensely orange-coloured complex ($K=10^{-31}$), which is called ferrioxamine (H. Keberle, Ann. N.Y. Acad. Sci., 1964; 119:758). A drastically reduced complexing occurs with iron(II) ions ($K=10^{-10}$). The protection which DFO forms against the formation of hydroxyl radicals lies in the complete enclosure of the bonded iron ions, in contrast to the complexing agent ethylenediaminetetraacetate, which still allows addition of an easily replaceable water molecule (E. Graf et al., J. Biol. Chem. 1984; 259:3620). As a result, the participation of the iron ion in the reaction cycle called the Fenton reaction (equation 1) with the formation of reactive hydroxyl radicals is suppressed.

$$Fe^{2+}+H_2O_2\text{- - - -}>Fe^{3+}+OH^-+OH\cdot \qquad (1)$$

Deferrioxamine has been used for than 20 years in treatment of severe ion poisoning, of disturbances in iron storage and of diseases which lead to increased iron values. Examples are idiopathic haemochromotosis, thalassaemia (hereditary disorder in globin synthesis of haemoglobin), sickel cell anaemia, frequent blood transfusions, excess iron absorption or haemolyses induced by medicaments. An accelerated wound contraction was also to be found in wound healing in animal studies after systemic administration of DFO (H. Cohly et al., Diabetes 1997; 46:295A). The low toxicity (J. B. Porter and E. R. Huens, Bailliere's Clin. Haematol. 1989; 2:257) and the low tendency to penetrate through biological membranes (J. B. Lloyd et al., Biochem. Pharmacol. 1991; 41:1361) make DFO an ideal active compound for trapping excess iron out of extracellular fluids. It is known from in vitro experiments that on incubation of dissolved DFO with ferritin and haemosiderin, iron can be dissolved out up to the maximum saturation of DFO. On incubation with iron-saturated transferrin, 10 to 15% of the iron can be dissolved out, while the iron cannot be removed from the porphyrin ring of haemoglobin and myoglobin (H. Keberle, Annu. N.Y. Acad. Sci. 1964; 119:758). In vivo, DO thus bonds only depot iron and—to a small extent—transport iron. Haemoglobin and myoglobin and iron-containing enzymes of the respiratory chain are not influenced. The high specificity for iron furthermore prevents the elimination of other metal ions essential for wound healing, such as magnesium, calcium and zinc.

Colonization and infection or poorly healing wounds by microorganisms is a major and frequently occurring problem in the treatment of wounds. Bacteria can trigger an excessive immune response and thus adversely influence the course of wound healing (M. C. Robson et al., Clinics in Plastic Surgery, 1990; 17:485). Chronic wounds are affected more often than acute wounds because of tissue which has already died (P. Mertz et al., Dermatologic Clinics 1993; 11;739). For example, a persistent colonization of a leg ulcer with *Staphylococcus aureus* led to an enlargement of the ulcer with the development of haemorrhagia and incipient necrosis (S. Munk et al., Acta Pathol. Microbiol et Immunol. Scand. 1996; 104:895; J. Danielsen et al., J. Wound Care, 1997; 6:308). The iron transport proteins transferrin and lactoferrin—the latter is also secreted from leukocytes—occurring in the serum have a potent bacteriostatic action by withdrawal of iron from bacteria, and therefore contribute towards controlling infections (R. Critchton, in: Inorganic Biochemistry of Iron Metabolism, 1991; Elis Horwood, New York, 101). A high-affinity iron chelator immobilized on a wound covering shows an analogous action, the growth of bacteria being inhibited and recolonization being made difficult.

In respect of ROS, in aerobic biological systems the dimeric or tetrameric enzyme superoxide dismutase (SOD) plays the main role in cell defence against the oxygen-mediated toxicity of ROS and in regulating the intracellular oxygen concentration (I. Fridovich, Annu. Rev. Biochem. 1995; 64:97). The ubiquitous enzyme catalyses the dismutation reaction of superoxide into less toxic hydrogen peroxide and oxygen (equation 2). SOD furthermore prevents reaction of superoxide with nitrogen monoxide, which is responsible for regulation of blood pressure (R. F. Furchgott, Nature 1980; 288:373). In eukaryotic cells, SOD is in the cytosol and in the mitochondria. The various enzymes with molecular weights from 32,000 to 56,000 Da have metal ions, such as copper and zinc (Cu—Zn—SOD), manganese (Mn—SOD) or iron (Fe—SOD) as co-factors in the catalytic centre.

$$2O_2^{-} + 2H^{+} \cdots \to H_2O_2 + O_2 \qquad (2)$$

The hydrogen peroxide formed by reaction of the SOD is then converted into water and oxygen in a multi-stage catalytic cycle by the redox enzyme catalase, which is ubiquitous in aerobic organisms (P. Gouet et al., Nature Structural Biology 1996; 3:951). In addition to catalase, the enzymes gluthathione peroxidase and myeloperoxidase are also capable of breaking down hydrogen peroxide. The most widespread form of catalase is a homotetramer (235,000 Da, bovine liver) with a porphyrinic group with one iron atom per sub-unit.

According to the invention, these abovementioned substances ("trapper molecules") are not administered per se, but are employed in a form covalently bonded to a wound covering. By fixing the "trapper molecules" to the wound covering, the site of action is precisely defined and is limited to the wound region or the wound fluid. A systemic action, i.e. an interaction with the entire organism, is avoided in this way. The action principle thus comprises a complexing, chelating or bonding reaction of the interfering factor or a chemical reaction with the interfering factor on the wound covering.

The present invention thus relates to novel wound coverings which impart an additional healing effect by the controlled removal or elimination of interfering factors, i.e. of substances which impede healing of chronic wounds.

The interfering factors can be removed or eliminated by a physical, chemical or immunological route. In particular, bonding or complexing or chelating of interfering factors is a preferred embodiment of the invention, since the interfering factors are removed finally from the wound region when the dressing is changed.

For such a wound dressing to function as intended, covalent bonding of the "trapper molecules" to the wound covering is of great importance. The carrier material of the wound covering according to the invention, i.e. the polymeric material (of natural or synthetic origin) to which the "trapper molecule" is covalently bonded, must be activatable for the coupling or, if this should not be the case, rendered activatable in a prior reaction. All carriers of materials which still carry functional groups such as e.g. —OH, —SH, —NH$_2$, —NHR, —CHO, —COOOH or —COOR on the surface after production of the wound covering can in principle be activated. The coupling steps then necessary can take place chemically or enzymatically, and are described in standard works as general immobilization techniques (J. M. S. Cabral and J. F. Kennedey in: Protein Immobilization—Fundamentals and Applications, 1991; p. 73, ed. R. F. Taylor, Marcel Dekker, New York; Immobilization of Enzymes and Cells, 1997; ed. G. F. Bickerstaff, Humana Press, Totowa, N.J.). However, it is also possible for the "trapper molecules" already to be bonded to starting materials which are employed for the production of the carrier material or the wound covering.

According to a preferred embodiment of the invention, polymers with activatable hydroxyl groups are the starting substances and are used either per se as the wound covering or as one of several components of a wound covering.

According to the invention, for example, the following carrier materials are possible: naturally occurring and modified and other forms of cellulose [such as e.g. carboxymethylcellulose, cellulose acetate and viscose fibres, bacterial cellulose (U. Geyer et al., Int. J. Biol. Macromol. 1994; 16:343)], alginates, hyaluronic acid, chitin or chitosans and other polysaccharides, such as e.g. Sephadex®, Sephacryl®, Sepharose® and Superdex®, synthetic polymers, such as e.g. polyamides, polyesters, polyolefins, polyacrylates, polyvinyl alcohols, polyurethanes and silicones, including mixtures and copolymers thereof, into which various functional groups, such as e.g. hydroxyl, carbonyl, carboxyl, amino or peroxy, can be introduced on the surface by corona treatment, plasma treatment or polymer grafting (chemical grafting) (D. M. Coates and S. L. Kaplan, MRS Bulletin 1996; 8:43). The abovementioned carrier materials can be employed as films, gels, foams, laminates and composites (mixtures).

The activation of the functional group for covalent coupling of proteins, antibodies, enzymes or low molecular weight organic substances via amino groups is described in detail in standard works, such as e.g. W. H. Scouten, Immobilized Enzymes and Cells, in: Methods Enzymol., ed. K. Mosbach, 1987; 135:30 and in: Immobilization of Enzymes and Cells, 1997; ed. G. F. Bickerstaff, Humana Press, Totowa, N.J. Functional amino groups which can be used in the case of proteins, antibodies and enzymes are the amino group of the amino terminus and/or the ε-amino groups of amino acid side chains of lysine and arginine exposed to the surface. Reagents such as, for example, 1,1'-carbonylditriazole, 1,1'-carbonyldiimidazole (CDI), cyanuric chloride, chloroformic acid esters, succinic anhydride, dicyclohexylcarbodiimide, p-nitrophenyl chloroformate, 2, 4, 5-trichlorophenyl chloroformate, p-toluyl chloride and tricresyl chloride can be employed for activation of hydroxyl groups which are on a soluble polymer (compare C. Delgado et al., Critical Reviews in Therapeutic Drug Carrier Systems, 1992; 9:249).

Corresponding coupling processes are known in the prior art and are employed e.g. in the preparation of substances for preparative and analytical uses. Thus, for example, EP 0 087

786 describes a process for immobilization of the iron chelator DFO via bonding of the primary amine group, DFO being bonded to agarose-polyaldehyde gel beads. The agarose was activated beforehand by periodate oxidation. The covalent bonding of DFO to dissolved biopolymers, such as dextran, hyaluronic acid, hydroxyethyl-starch, methylcellulose, inulin and human serum albumin, is furthermore described in EP 0 304 183. In this case, the terminal amine function of the DFO is coupled with an aldehyde group of the polysaccharide to give a Schiff's base, and is then reduced with sodium borohydride, as described by S. Margel and E. Weisel (J. Pol. Chem. Sci., 1984; 22:145) and EP 0 087 786. Other medicaments or proteins can also be coupled covalently to agarose-polyaldehyde gel beads via the reaction of primary amine or thiol groups with the aldehyde groups. WO 96/39125 describes a matrix comprising a high-viscosity cubic phase of e.g. amphiphilic glyceryl monooleate, in which horseradish peroxidase or catalase is embedded. This matrix represents a barrier between the enzyme bonded in this manner and external proteolytic enzymes or cell defence systems of the patient and thus prevents release of the enzyme. The catalytic activity of the enzyme remains accessible to the particular substrate through pores and channels in the matrix. M. M. Hossain and D. D. Do (Biotechnology & Bioengineering, 1988; 31:730) describe the immobilization of the enzyme catalase on glass particles of controlled pore size and subsequent kinetic measurements. The covalent modification of SOD (P. Pyatak et al., Res. Com. Chem. Path. and Pharmacol., 1980; 29:115) and CAT (A. Abukovski et al., J. Biol. Chem., 1976; 252:3582) and other enzymes (M. L. Nucci et al., Advanced Drug Delivery Reviews, 1991; 6:133) with polyethylene glycol by coupling of activated polyethylene glycol on to amino groups of the enzyme is described. H. Hirane et al. (J. Controlled Release, 1994; 28:203) describe the preparation of SOD polymer conjugates with activated divinyl either and maleic anhydride. WO 95/15352 describes covalent bonding of peroxidase and catalase via amino groups into a polymer gel comprising the protein BSA and preactivated polyethylene glycol. G. Maneke and D. Polakowski (J. Chrom., 1981; 215:13) describe the immobilization of α-chymotrypsin on a polymer matrix of polyvinyl alcohol and terephthalaldehyde The prior art has not described to date the use of substances which interact with interfering factors which are present in wound exudate and impede the wound healing process for the production of wound coverings. By analogous use of the abovementioned coupling processes, the substances which interact with the interfering factor are coupled covalently according to the invention on to carrier materials suitable for wound coverings by chemical reaction and novel wound coverings are produced in a controlled manner for selective removal of interfering factors from the wound fluid of wounds which heal poorly or not at all. The present invention provides for the first time novel wound coverings for improving the healing course of these wounds.

Possible wound coverings are, for example, wound coverings from the group consisting of dressings, dressing gauze, bandages, compresses, cotton-wool, patches, foils, films, hydrocolloid dressings, gels and the like.

In the context of the present invention, the wound coverings known in the prior art can thus be used and can be modified according to the invention by covalent bonding of "trapper molecules". Thus, in particular, wound coverings which absorb moisture can be used. Furthermore, it is of course possible to apply simultaneously with the wound coverings according to the invention wound healing-promoting substances, such as e.g. growth factors (e.g. PDGF), regulatory cytokines, peptides and hormones, which are suitable for promoting wound healing or accelerating the healing process, into the wound.

The present invention is explained in the following with the aid of examples and figures:

EXAMPLES

EXAMPLE 1

Immobilization of DFO on Cellulose

Figure 1:
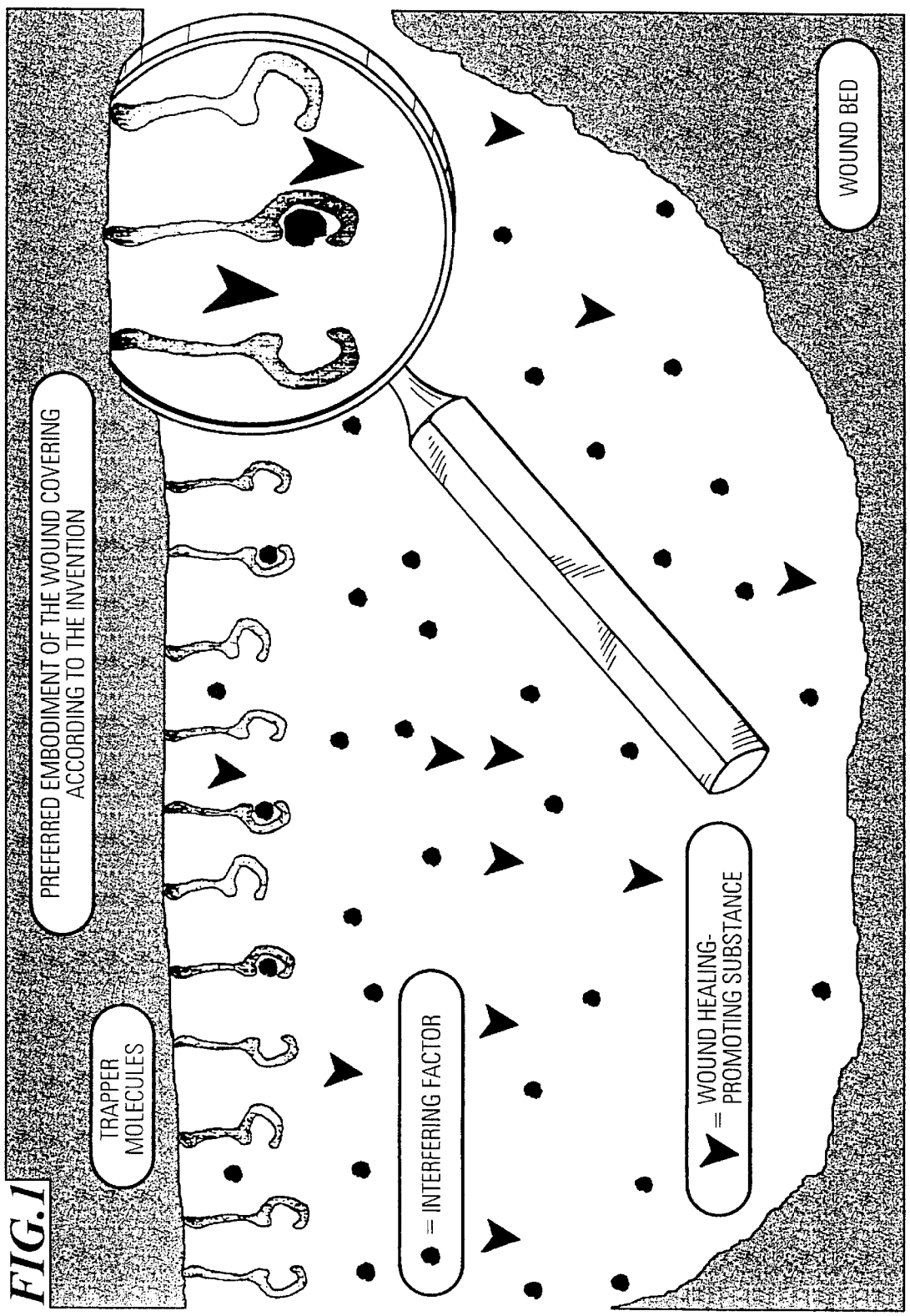
FIG. 1 is a diagram of a particular embodiment of the invention in which selective bonding of the interfering factors to the trapper molecules is shown.
Figure 2:
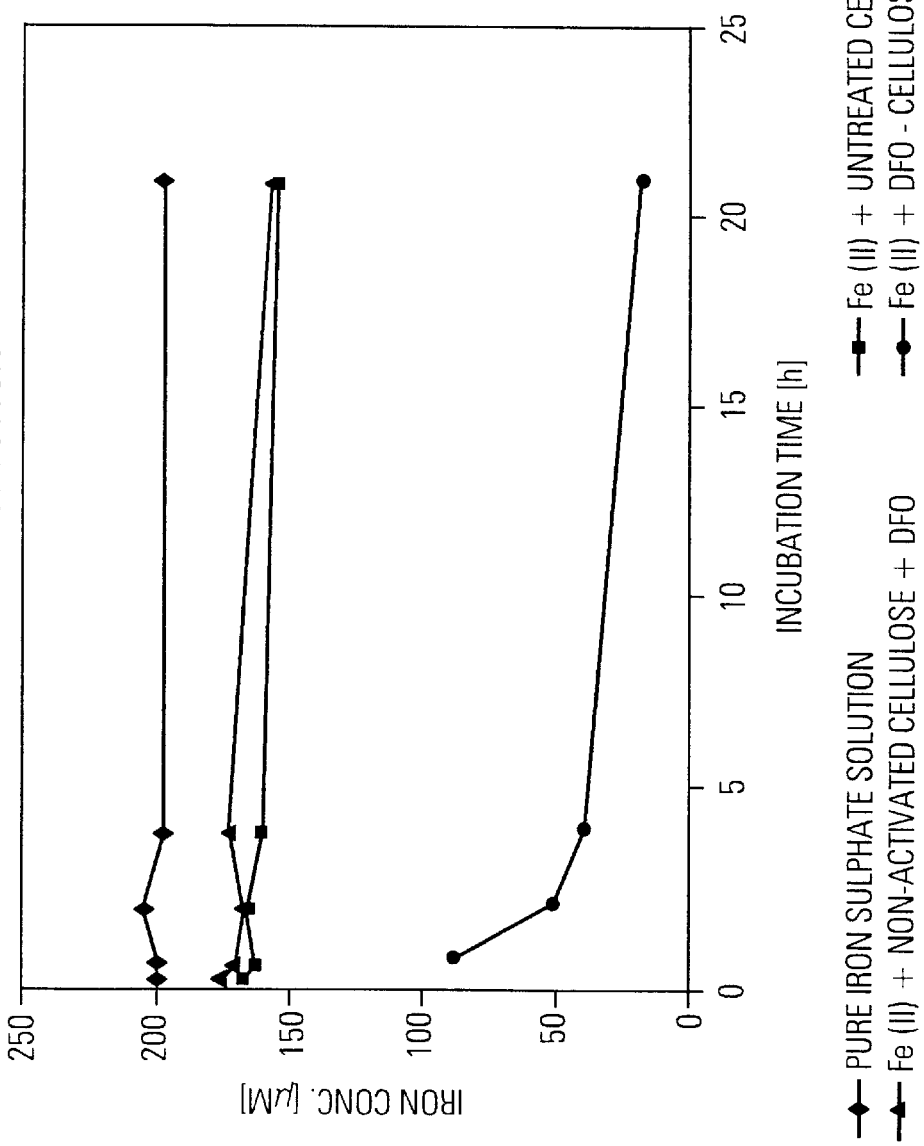
FIG. 2 is a graph of the kinetic course of the complexing of dissolved iron by DFO immobilized on medicinal dressing cotton. Within the first 2 h the majority of the iron available is bonded by the DFO wound covering. After incubation for 2 h 75% and after incubation for 24 h 92% of the iron available from the solution is complexed. The iron-bonding capacity of the DFO-cellulose sample employed is a maximum of 380 μmol iron/g sample, after incubation overnight. The non-activated or completely untreated cellulose controls and the pure iron solution show no significant decrease in iron in the supernatant.
Figure 3:
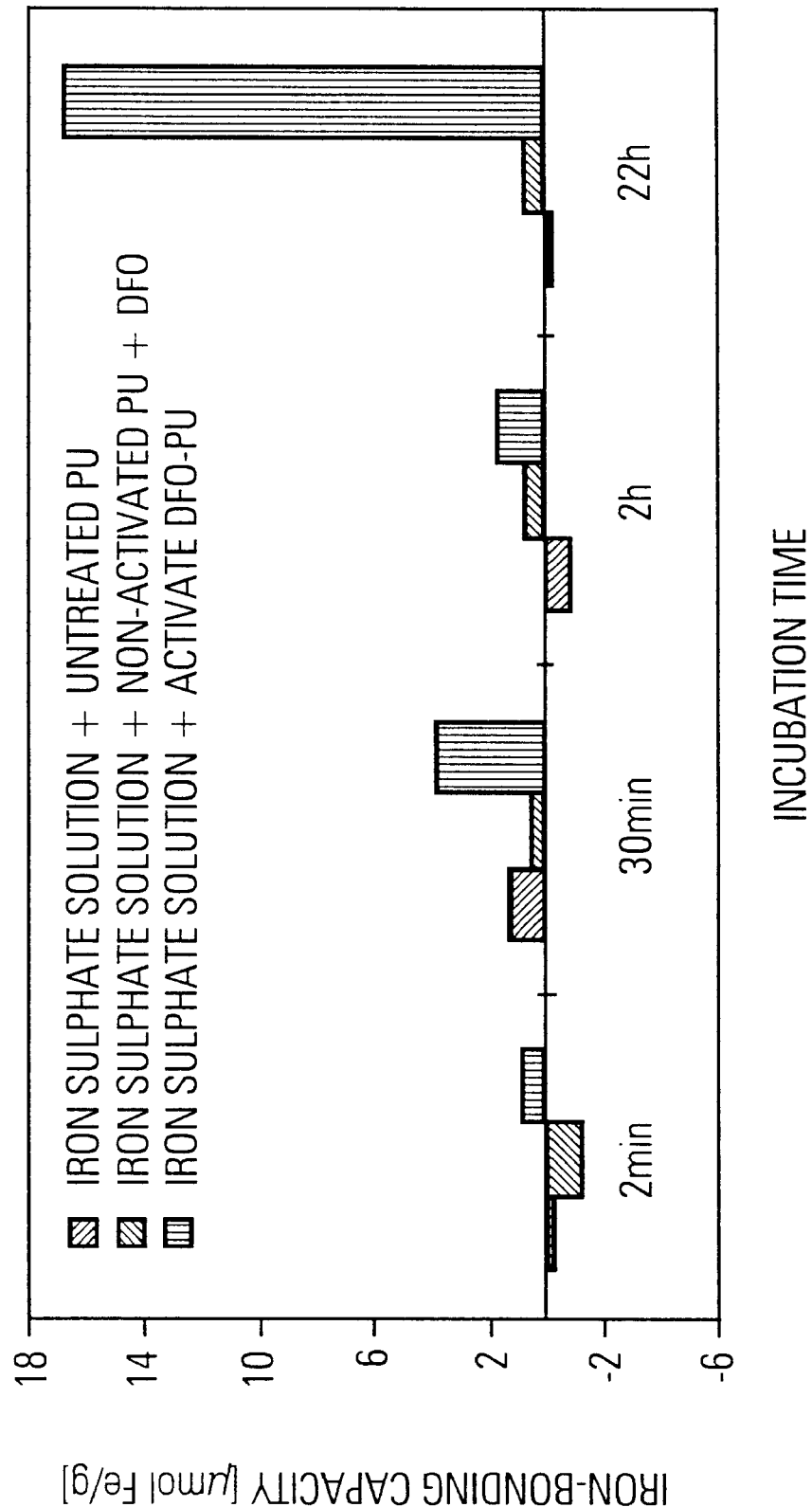
FIG. 3 is a graph of the course of the complexing of dissolved iron by DFO immobilized on polyurethane as function of time. After incubation overnight, an iron-bonding capacity of 17 μmol iron/g polyurethane is achieved. The controls also run (untreated and non-activated polyurethane) who no significant iron-bonding behaviour.
Figure 4:
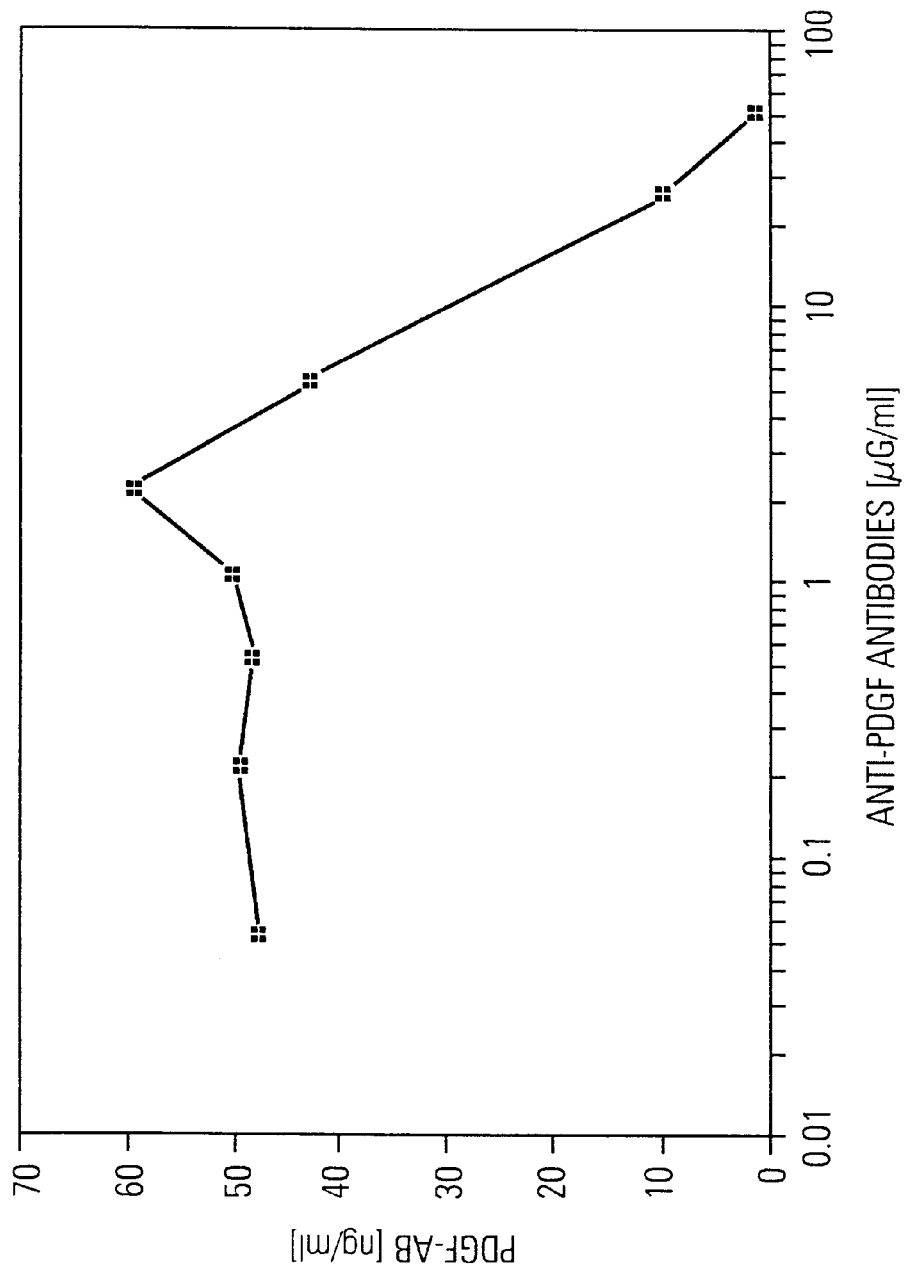
FIG. 4 shows the selective bonding of PDGF-AB with a concentration of 50 ng/ml by anti-PDGF antibodies immobilized on cellulose.

The experiments for immobilization of deferrioxamine (DF)) on cellulose were carried out as follows: 5 g of a medicinal dressing cotton (Gazomull®, Beiersdorf AG) were boiled in 100 mM bicarbonate buffer for 30 min, subsequently rinsed 2 l water, dried in air and finally dewatered by addition of dry acetone and dried in a vacuum concentrator (Bachhofer, Reutlingen) on watch-glasses at room temperature for 60 min. The dressing cotton was then activated with 5 g 1,1'-carbonyldiimidazole (CDI; Fluka, Buchs) (freshly prepared in 500 ml dry acetone) under reflux at 60° C. for 60 min (1% CDI solution). Excess CDI was removed by washing with acetone.

The acetone was removed from the dressing cotton in subsequent transfer baths with acetone-water mixtures of 3:1, 1:1 and 1:3 and by drying in air. The coupling reaction of DFO on the activated dressing cotton was carried out in a glass column (Pharmacia, Uppsala) with the dimensions 2.6 cm ×40 cm. For this 3.28 g deferrioxamine mesylate (DFOM) (Sigma, Munich) were dissolved in 500 ml bicarbonate buffer (100 mM, pH 8.5) (which gave a concentration of 10 mM) and passed through the column in circulation from the bottom upwards at a flow rate of 10 ml/min using a peristaltic hose pump (Ismatec, Munich). Coupling was carried out for 18 h at room temperature with an aluminium foil jacket on the glass column. Non-bonded DFO was removed from the dressing cotton by washing several times with bicarbonate buffer (25 nM, pH 8.5). Finally, the piece of cellulose-DFO was dried in air.

The cellulose-DFO adducts were analyzed in respect of the amount of immobilized DFO and characterized as described below.

Quantification of the amount of DFO immobilized on the dressing cotton using HPLC and spectroscopy gave values of 30 to 50 µmol/g. The immobilized DFO was saturated with iron (called DFO—Fe) and the release of iron from DFO—Fe was determined as 5 to 10 µmol/g with gallium (III) under reductive conditions. The iron-bonding activity was determined by incubation of a 50 mg sample in 30 ml of a solution comprising 0.2 mM $FeSO_4$ (120 µmol/g), 1 mM $MgCl_2$, 1 mM $CaCl_2$ and 154 mM NaCl with a pH of 5.6 for 2 hours. An iron uptake of the amount of iron available of 38 µmol/g (32%) was found, compared with 4 µmol/g (3%) from untreated cellulose and non-activated cellulose/DFO as the control.

EXAMPLE 2

Immobilization of DFO on a Cellulose Sponge 500 mg of a pressed piece of regenerated cellulose (Cellspon®, Cellomeda Oy, Turku) with a thickness of 2 mm were boiled in bicarbonate buffer (120 mM, pH 8.5) for 30 min, rinsed with water, dried in air and then dewatered with absolute acetone and dried in vacuo. The activation with 500 mg (3.08 mmol) CDI in 50 ml absolute acetone was carried out in a 100 ml glass flask at 60° C. under reflux for 60 min. Excess CDI was removed by washing with acetone, and this in turn was removed with acetone-water transfer baths (see above) and by drying in air. Coupling with 250 mg (0.38 mmol) DFOM was carried out in 40 ml bicarbonate buffer (100 mM, pH 7.7) in 50 ml screw-top vessels (Greiner, N ürtingen) with intensive thorough mixing. After 18 h, the coupling reaction was stopped and the piece of Cellspon® was washed several times with 100 mM and 500 mM bicarbonate buffer and water until no DFO was detectable from the piece. Finally, the Cellspon® piece coupled with DFO was dried in air and stored in screw-top vessels at room temperature.

Measurement of the amount of DFO immobilized on Cellspon® using HPLC and spectroscopy (see below) gave values of 35 to 70 µmol/g. The release of iron from DFO—Fe showed values of 15 to 40 µmol/g. The iron-bonding activity was determined as described in example 1. An iron uptake comparable to that with dressing cotton was found.

EXAMPLE 3

Immobilization of DFO on Levagel 6.4 g (1 mmol) Levagel (Bayer, Leverkusen), a copolymer of propylene oxide and ethylene oxide with a molecular weight of 6,400 g/mol, were dissolved in 50 ml absolute acetone in a round-bottomed flask under nitrogen as an inert gas, while stirring. 160 mg (1 mmol) CDI, also dissolved in 50 ml absolute acetone in a dropping funnel, were added to this over a period of 20 min. After 60 min the solvent was distilled off in a rotary evaporator (Heidolph, Kehlheim) and the CDI-activated Levagel was further reacted immediately. For the coupling reaction, 250 mg (40 µmol) CDI-activated Levagel were dissolved in bicarbonate buffer (250 mM, pH 8.5) with 30% ethanol, since Levagel forms an emulsion in aqueous systems. 87.5 mg (135 µmol) DFOM were dissolved in 13.5 ml bicarbonate buffer and the solution was stirred at room temperature for 12 h. The reaction mixture was then introduced into a dialysis hose (Spektrapor, Serva) with an exclusion volume of 3,500 Da an dialysed twice for 8 h against in case one liter phosphate buffer/ethanol. Because of the molecular size, only low molecular weight substances, such imidazole, salts and unreacted DFO, can pass through the pores of the dialysis membrane, while Levagel and Levagel-DFO remain in the membrane.

EXAMPLE 4

Immobilization of DFO on a Polyurethane Gel the polyurethane gels (PU gel) comprise a Levagel component and a diisocyanate component, such as, for example, hexamethylene diisocyanate, hexahydrophenylene 1,3- and/or 1,4-diisocyanate or perhydrotoluyl 2,4'- and/or 4,4'-diisocyanate with an NCO/OH ratio of 0.3 to 0.7. Since not all the OH functions react during the crosslinking process, the same activation and coupling reactions can proceed on the surface of the polyurethane gel as on the free Levagel.

A PU piece of 14 g (5×5 cm, 0.5 cm thick), which approximately corresponds to 2.2 mmol Levagel, was placed in 75 ml absolute acetone in a glass flask with exclusion of moisture, and 355 mg (2.2 mmol) CDI were added. The PU piece was activated under reflux at 50° C., while stirring and with exclusion of air, for 40 min. During this procedure, the PU piece swelled by approx. 50% due to penetration of acetone and CDI dissolved therein. After the activation reaction, the PU piece was briefly washed several times with acetone in order to remove excess CDI and the imidazole formed. Thereafter, the PU piece was placed in a vacuum concentrator for 1 h and the solvent acetone was withdrawn, with shrinkage. 1.4 g DFOM (2.2 mmol) in 75 ml bicarbonate buffer (100 mM, pH 8.5) were immediately added to the CDI-activated PU gel and the mixture was stirred at room temperature for 18 h. The PU—DFO gel formed was then washed 3 times with bicarbonate buffer (25 mM, pH 8.5), dried in air and stored at 4° C. in a glass dish closed with Parafilm (American Can Company, Greenwich).

The quantification of the amount of DFO immobilized on a PU gel using HPLC and spectroscopy gave values of 45 µmol/g. The release of iron from PU—DFO—Fe as described below showed coupling yields of 8 mol DFO/g, in contrast to non-activated PU gel, from which the amount of iron released was 0.2 µmol DFO/g. The iron-bonding capacity was determined as 17 µmol DFO/g, compared with 0 µmol DFO/g of the untreated PU and 0.8 µmol DFO/g of the non-activated PU/DFO.

EXAMPLE 5

Immobilization of DFO on a Polyurethane Film

A 30 $cm^2$ piece of a polyurethane film (PU film) with a thickness of 30 µm and a weight of 130 mg was introduced into a glass flask and covered with a layer of 20 ml absolute acetone. 30 mg (185 µmol) CDI in 20 ml absolute acetone were added dropwise in the course of 5 min, while stirring, and the mixture was kept under reflux at 50° C. for 30 min. After the CDI activation step, the acetone mixture was poured off and the activated film was washed several times with acetone, and 120 mg (183 µmol) DFOM, dissolved in 50 ml bicarbonate buffer (100 mM, pH 8.5) were added immediately. After 12 h, the PU film was taken out of the reaction mixture and washed several times with de-ionized water, until the colour detection for DFO with iron sulphate solution was negative. The PU—DFO film was dried in air and stored in a closed glass dish.

Functionality Assay of the Immobilized DFO with Iron

By complexing iron with dissolved DFO, the intensely orange-coloured DFO-iron(III) complex ferrioxamine is formed (P. E. Hallaway et al., PNAS 1989; 86:10108). Incubation of the DFO-coupled matrices with 5 mM iron sulphate (pH 5.0) or iron chloride (pH 2.2) solution leads to an orange coloration of the dressing cotton within a few minutes, the sample with iron sulphate solution being dyed more slowly than that with iron chloride solution. This effect is to be attributed to a ferroxidase property of the DFO molecule, which oxidizes $FE^{2+}$ to $Fe^{3+}$ before complexing of the iron (J. F. Goodwin and C. F. Whitten, Nature 1965; 205:281).

After leaving to stand overnight, an intensification of the colour of the samples prepared according to the above examples occurred. For visual characterization of the DFO-coupled samples, in each case 100 mg dressing cotton coupled to DFO, pure dressing cotton and non-activated dressing cotton which was treated with DFOM solution, were incubated as described above with in each case 5 ml of a 5 mM iron sulphate or iron chloride solution in 50 ml plastic screw-top vessels (Greiner, Nürtingen) for 18 h in an overhead shaker (Heidolph, Kelheim), and the colorations established were evaluated.

Methods for Quantification of the Total Immobilized DFO

Spectroscopic Quantification in Solution

By determining the concentration of dissolved DFO in the coupling solution before and after the reaction and in the combined was solutions, the amount of immobilized DFO can be determined by calculating the difference. For this, an aliquot of the DFO solution is converted into the iron-bonded form, ferrioxamine, with a 10-fold excess of $FeCl_3$. After an incubation time of 30 min, the absorption is measured at 430 nm in a Uvikon 943 Photometer (Kontron, Neufarn). The DFO concentration is calculated via the Lambert-Beer Law ($\epsilon = \epsilon \cdot c \cdot d$; E=extinctions [-], c=concentration of DFO [mol/l], d=cell layer thickness [cm] and $\epsilon$=specific molar extinction coefficient of ferrioxamine, 2,300 $M^{-1} \cdot cm^{-1}$). The saturation of the dissolved DFO with iron can be achieved equally with an iron sulphate solution (P. E. Hallaway et al., PNAS 1989; 86:10108). However, in this case incubation must be carried out for a longer period of time, so that the DFO—Fe(II) complex initially formed is converted into the more stable DFO—Fe(III) complex. To achieve an accurate and reproducible determination of the DFO concentration, it is necessary for all the DFO solutions to be measured to have the same buffer composition.

Quantification by HPLC

The concentration determinations on DFO were carried out by means of a Nucleosil C18 reversed-phase column (Macherey & Nagel, Düren) of dimensions 125 cm×4 mm and an HPLC unit from Pharmacia (Pharmacia LKB, Uppsala), pump model 2249 and monitor model VWM 2141 at a detection of 430 nm. For calibration, in each case a 20% excess of an iron chloride solution was added to various DFOM standards (10 and 1 mM) in bicarbonate buffer (25 mM, pH<6) and, after incubation for 30 min, the samples were introduced at a flow rate of 1 ml/min on to the column, which had been equilibrated with potassium phosphate buffer (30 mM, pH 3.5). After a linear gradient of from 0 to 25% acetonitrile within 9 min had been started, ferrioxamine was eluted at 8.7 min. The DFO samples to be measured were prepared analogously. To calculate the amount of DFO bonded, the DFO concentration of the supernatant after the coupling reaction and the DFO concentration in the combined wash solutions were subtracted from the coupling concentration (10 mM).

Method for Quantification of the Immobilized DFO with an Iron-bonding Activity

Pieces (50 to 100 mg) of dressing cotton coupled with DFO or polyurethane coupled with DFO were incubated in screw-top vessels of plastic with in each case 10 to 40 ml of a solution of iron sulphate (0.2 mM), $CaCl_2$ (1 mM), $MgCl_2$ (1 mM) and NaCl (155 mM) in an overhead shaker for a period of 24 h. The decrease in iron in the supernatant with respect to time was determined spectroscopically at 562 nm with the aid of the MPR 3 ready-to-use assay for iron (Boehringer, Mannheim). At least 3 samples of one type were measured, and the supernatant was in each case subjected to a triplicate determination. Iron which had not been complexed by DFO was bonded by ferrozine (3-(2-pyridyl)-5,6-diphenyl-1,2,4-triazine-p,p'-disulphonic acid) to form a violet complex (with an absorption maximum at 562 nm and a molar extinction coefficient of 29,000 $M^{-1}$ $cm^{-1}$). The iron-ferrozine complex has an extinction coefficient which is higher by a factor of ten compared with the iron-DFO complex, which allows a very sensitive detection limit of <10 μM iron. Pure iron sulphate, untreated dressing cotton (or untreated polyurethane) and non-activated dressing cotton (non-activated polyurethane), which were treated according to the coupling conditions, served as the control. The amount of immobilized DFO could be concluded from the difference between the amount if iron before and after incubation with the DFO samples.

Method for Release of Iron from Immobilized DFO-iron (DFO—Fe)

This method is based on the method described by T. Emery (Biochemistry 1986; 25:4629) and is used for detection of iron complexed by DFO. For this, DFO immobilized on a matrix was incubated with an iron chloride solution (10 mM) for 10 min at room temperature and converted completely into the iron-bonded form. Thereafter, non-bonded iron was washed out of the matrix with 20 mM acetate buffer (pH 5.4) until the detection of iron in the wash buffer using ferrozine revealed no further coloration. Finally, the iron(III) complexed by DFO was displaced from the immobilized DFO by 20 mM ascorbate and 20 mM gallium(III) nitrate in 100 mM acetate buffer (pH 5.4), with reduction of the iron and bonding of Ga(III) by DFO. The iron(II) released in this way was bonded as an iron(II) complex by the complexing agent ferrozine (4 mM) and the violet-coloured solution was determined quantitatively at 562 nm. The value of the control of the non-coupled matrix was in each case to be subtracted from the iron value measured.

Method for Measuring the In Vitro Uptake of Iron from Serum and Wound Fluid

Fresh donor blood filled in plastic tubes coated with heparin was separated into plasma and serum by centrifugation in a centrifuge for 5 min at 10,000 rpm. One ml of the serum sample was pipetted into a microtube (Eppendorf vessel) and temperature-controlled at 37° C. Thereafter, 0.1 μM free DFOM, in each case 10 mg dressing cotton, DFO-coupled dressing cotton, PU and DFO—PU were added and the samples were incubated in a temperature-controlled shaking apparatus for up to 24 h. The total amount of iron in the serum sample was determined at various points in time with the aid of the MPR 3 iron kit from Boehringer Mannheim. In this, the content of non-bonded iron which remained was determined by dissolving iron(III) in a detergent mixture of transferrin in a weakly acid pH range and reducing it to iron(II) with ascorbate. The colour complex formed with ferrozine was quantified by spectroscopy.

EXAMPLE 6

Immobilization of SOD or Catalase on Cellulose

The various immobilization reactions of superoxide dismutase (SOD, EC 1.15.1.1) and catalase (CAT, EC 1.11.1.6)

were carried out with the following enzymes: Cu, Zn—SOD from bovine erythrocytes (Boehringer Mannheim), Fe—SOD and Mn—SOD from *E. coli* (Sigma, Munich), Cu, Zn—SOD from horseradish (Sigma, Munich), SOD from yeast with the tradename Distmutin-BT® (Pentapharma, Basel) and catalase from bovine erythrocytes (Boehringer Mannheim). For this, medicinal dressing cotton (Gazomull®, Beiersdorf AG) was boiled as already described above and activated with CDI. Pieces (0.5 g) of the CDI-activated dressing cotton were incubated with 20 ml bicarbonate buffer (100 mM, pH 8.5) with enzymes solutions of 1 to 50 mg/ml in 50 ml plastic screw-top vessels (Greiner, Nürtingen) at room temperature for 16 h, while shaking in an overhead shaker (Heidolph, Kehlheim). The supernatants of the coupling solutions were then transferred in to new plastic screw-top vessels and stored at 4° C. for the analysis. Thereafter, they were washed three times with in each case 30 ml bicarbonate buffer (100 mM, pH 8.5) and finally with 30 ml bicarbonate buffer (100 mM, pH 8.5) and sodium chloride (500 mM), in order to remove non-bonded protein from the dressing cotton. The coupling and wash buffer for catalase was brought to a pH of 8.0. Residual imidazolyl groups of the cellulose which had not yet reacted were blocked by incubation with 25 ml glycine (200 mM) in bicarbonate buffer (100 mM, pH 8.5) in plastic screw-top vessels at room temperature in an overhead shaker for 16 h. The cellulose treated in this way was then washed five times with in each case 30 ml bicarbonate buffer (100 mM, pH 8.5), and then twice with 30 ml 0.9% sodium chloride solution and three times with 30 ml deionized water (Millipore, Bedford). Finally, the cellulose coupled with enzyme was dried in air in half-opened Petri dishes in a fume cupboard for 2 h, packed in a cellophane bag and stored at 4° C.

EXAMPLE 7

Immobilization of SOD and CAT on a Cellulose Sponge 500 g of a pressed cellulose piece (Cellspon®, Cellomeda Oy, Turku) with a thickness of 2 mm were boiled in 120 mM bicarbonate buffer for 30 min and then dewatered with absolute acetone and dried in vacuo. Activation with 500 mg (3.08 mmol) CDI in 50 ml absolute acetone was carried out in a 100 ml glass flask at 60° C. for 60 min under reflux. Excess CDI was removed by washing with acetone, and this in turn was removed with acetone-water transfer baths (see above) and by drying in air. Coupling with 250 mg (7.7 µmol) SOD or 300 mg (1.2 µmol) CAT was carried out in 40 ml bicarbonate buffer (100 mM, pH 7.7) in 50 ml screw-top vessels (Greiner, Nürtingen), with intensive thorough mixing. After 18 h, the coupling reaction was stopped and the mixture was washed several times in succession with 100 mM and 500 mM bicarbonate buffer and finally with water, until non-bonded enzyme was no longer detectable. Finally, the Cellspon® piece coupled with enzyme was dried in air and stored at room temperature in screw-top vessel.

EXAMPLE 8

Immobilization of an Anti-PDGF Antibody on Cellulose

A 10×10 cm (2 g) piece of dressing cotton (Gazomull®, Beiersdorf AG) was activated with CDI as described above and washed. 7.5 mg of a monoclonal anti-PDGF antibody which originates from a mouse hybridoma cell line (cf. PCT/EP93/02295; column 12, lines 27–32) were then dissolved in 30 ml bicarbonate buffer (100 mM, pH 8.5) and the solution was added to the CDI-activated dressing cotton. The antibody specifically recognizes the B chain of the PDGF dimer. After incubation at room temperature for 24 h in a plastic Petri dish on a tilting table (Tecnomara, Zurich), the coupling reaction was processed as described above. Finally, the samples were washed several times with water and the dressing cotton coupled with antibody was dried in air at room temperature in half-opened Petri dishes in a fume cupboard for 2 h, packed in a cellophane bag and stored at 4° C.

The amount of anti-PDGF antibody bonded to the dressing cotton was determined by a bonding assay by measuring the antibody titer in the supernatant before the coupling and subtracting the titer after the coupling and in the wash solutions. Various concentrations of dissolved anti-PDGF antibody served as the control.

For this, PDGF—AB (50 µg/ml) in sodium bicarbonate buffer (200 mM, pH 7.8) was bonded (50 µl per depression) to a microtiter plate (Nunc, Weisbaden), blocked with 1% BSA solution (bovine serum albumin fraction V, Boehringer Mannheim, order number 775 860) in TBS buffer (50 mM TRIS, 150 mM NaCl, pH 7.5, Carl Roth Karlsruhe) and, after washing three times with TBS buffer with 0.1% Tween® 20 (poly(oxyethylene)$_n$ sorbitan monolaurate, order number 1 332 465, Boehringer Mannheim) (50 mM Tris, 150 mM NaCl, pH 7.5, Carl Roth, Karlsruhe), was incubated with 200 µl of the corresponding antibody solutions for two hours at room temperature. Thereafter, washing was carried out again three times with TBS buffer with 0.1% Tween® 20 and then incubation with a goat anti-mouse IgG-(H+L)-horseradish peroxidase conjugate (Bio-Rad, Munich, order number 170 6516) as a secondary antibody in a dilution of 1:1,000 for a further two hours. After washing three times with TBS buffer and washing once with sodium phosphate buffer (20 mM, pH 6.8), the sample was stained with 0.7 mg/ml 5-aminosalicylic acid (Sigma, Munich) and 0.5 µl/ml 30% hydrogen peroxide solution (Merck, Darmstadt) for 15 minutes, and the reaction was stopped with 100 µl 2 N sodium hydroxide solution per depression. The evaluation was carried out with an ELISA reader (Dynatech MR 5000, Denkendorf) at 450 nm and showed coupling yields of 100 to 200 µg anti-PDGF antibody/g.

EXAMPLE 9

Immobilization of Trypsin Inhibitor from Soya Beans on Cellulose

A 10×10 cm (2 g) piece of dressing cotton was activated with CDI as described above and washed. 20 mg trypsin inhibitor from soya beans (type I-S, Sigma, Munich), dissolved in 20 ml bicarbonate buffer (100 mM, pH 8.5), were then added to the activated dressing cotton and the sample was incubated in a plastic Petri dish at room temperature for 24 h on a tilting table (Tecnomara, Zurich). Processing of the coupling reaction was carried out as described above. Finally, the sample was washed with water. The cellulose coupled with protease inhibitor was dried in half-opened Petri dishes in fume cupboard for 2 h at room temperature, packed in a cellophane bag and stored at 4° C.

Method for Determination of Immobilized Protein

For qualitative detection of immobilized SOD on dressing cotton, this was investigated with the aid of immunofluorescence microscopy (IFM). All the incubation steps were carried out at room temperature. The antibody dilutions and washing steps were all carried out with PBST buffer (phosphate-buffered sodium chloride solution with 0.1% Tween® 20). Pieces with a size of in each case 1 cm² of the untreated dressing cotton and the dressing cotton linked covalently with SOD were blocked with 3% goat normal serum (DAKO, no. X 0907) in PBS (phosphate-buffered sodium chloride solution) for 1 h and washed twice. The dressing cotton samples were then incubated with a rabbit anti-SOD antibody (Biotrend, no. 100-4191) in a dilution of 1:100 for a further hour. After four washing steps, incubation with fluorescence-labelled goat anti-rabbit (IgG(H+L)*Cy2 (Dianova, No. 111-225-003) in a dilution of 1:200 with exclusion of light was carried out for one hour. The preparations were washed six times, covered with cover glasses and fixed with a solution of 30 mg 1,4-diazabicyclo[2.2.2] octane (DABCO; Sigma, no. D-2522) per ml MOWIOL fixing substance (Calbiochem, no. 475904) on microscope slides. Examination under the microscope was carried out with a Zeiss Axioscope in phase contrast and fluorescence mode (FITC filter).

Method for Quantification of Dissolved and Immobilized Protein

To determine the concentration of dissolved and immobilized protein, the BCA protein assay of Pierce (Rockford, Ill.) was used. In this, copper(II) ions are reduced to copper (I) ions by protein in an alkaline medium by the biuret reaction (R. E. Brown et al., Analytical Biochemistry 1989; 180:136). Within a concentration range of 20 to 2,000 μg/ml, the amount of reduced copper is proportional to the protein concentration. The soluble copper detection reagent biquinoline-4-carboxylic acid (BCA) then reacts with the reduced copper(I) ion to give a purple-coloured complex, the absorption maximum of which is at 562 nm.

For determination of protein immobilized on dressing cotton, the method published by T. M. Stich (Analytical Biochemistry 1990; 191:343) was largely adopted. Other protein determination methods, such as that of M. M. Bradford and O. H. Lowry, show bonding of the chromophor to the matrix. The BCA protein assay with protein immobilized on dressing cotton was carried out in a tissue culture plate (Greiner, Nürtingen). The dressing cotton with coupled protein was incubated in pieces of 20, 30 and 40 mg in the cavities of the tissue culture plate in a total volume of 1.68 ml (80 μl sample and 1.6 ml BCA solution) for 45 to 60 min at 37° C. or at 60° C. To determine the concentration of the immobilized protein, the particular dissolved protein was also incubated in a dilution series of 125 to 1,500 μg/ml as a standard. Finally, the tissue culture plate was measured and evaluated at 562 nm in a Microplate Reader model MR 5000 (Dynatech, Denkendorf).

Method for Determination of the Activity of Dissolved SOD

The Biotech SOD-525 assay (OXIS International S.A., France) was used for measurement of the activity of the various SOD enzymes. This assay is based on the SOD-induced increase in the rate constant of the auto-oxidation reaction of the catechol 5,6,6a,11b-tetrahydro-3,9,10-trihydroxybenzo[c] fluorene (BXT-01050) in aqueous alkaline solution (C. Nebot et al., Analytical Biochemistry 1993; 214:442). This auto-oxidation reaction generates a chromophor with a maximum absorption at 525 nm.

The assay was carried out in an air-saturated buffer with 50 mM 2-amino-2-methyl-1,3-propanediol, 0.1 mM diethylenetriaminepentaacetic acid and 3 mM boric acid, pH 8.8, at 37° C. The kinetics were measured at 525 nm within one minute after addition of BXT-01050. The SOD activity was determined by determining the ratio $V_s/V_c$ of the rate constants of the auto-oxidation reaction, the rate constants V being measured in the presence ($V_s$) and in the absence ($V_c$) of the sample. One SOD unit (SOD-525) is defined as the activity which doubles the background of the auto-oxidation reaction, that is to say $V_s/V_c=2$. The volume activity (SOD) in SOD-525 units/ml is evaluated after determination of $V_s/V_c$ via the following equation (given by the manufacturer):

$$(SOD) = \frac{0.93(V_s/V_c - 1)}{1.073 - 0.073(V_s V_c)}$$

Method for Determination of the Activity of Dissolved CAT

Catalase (EC 1.11.1.6, Boehringer Mannheim) catalyses the cleavage of hydrogen peroxide ($H_2O_2$) in oxygen and water. The activity of the dissolved enzyme is determined with a spectrophotometric assay modified according to R. F. Beers and I. W. Sizers (J. Biol. Chem. 1952; 195:133). The decrease in extinction at 240 nm here correlates with the decrease in hydrogen peroxide in the reaction mixture caused by catalase.

3 ml phosphate buffer (50 mM, pH 7.0) (reference position) or 3 ml of a phosphate buffer to which $H_2O_2$ had been added (0.05 mM $H_2O_2$, pH 7) (sample) with in each case 0.05 ml of the catalase-containing sample were introduced into a quartz cell (Hellma, Jena). The hydrogen peroxide concentration in the $H_2O_2$-containing buffer was checked by extinction measurement at 240 nm, the absorption thereof being at 0.500±0.01. After the components had been mixed in the quartz cells (layer thickness (10 mm), the reaction was observed until the extinction had reached a value of 0.450. From this point, the time required to reduce the extinction to 0.400 was recorded with a stopwatch. The enzyme concentration in the cell was adjusted so that the time required for this was 20±2 seconds [s].

The volume activity was calculated according to the following equation:

Volume activity [U/ml]=(17·13)/time recorded [s]·0.05

Total activity of the sample [U]=Volume activity [U/ml]
·dilution·sample volume [ml].

One unit [U] is defined here as that enzyme activity which disproportionates 1 μmol hydrogen peroxide under the chosen assay conditions (25° C., pH 7.0) per minute.

Method for Determination of the Activity of Immobilized Enzyme, Antibody and Protein SOD Immobilized on Cellulose The determination of the immobilized SOD (cf. L. Goldstein, Meth. Enzym., 1976; 44:397) was carried out in principle by the same assay principle as has been described above for the dissolved enzyme. It was necessary to adapt the apparatus to the measurement operation. Instead of the quartz cell, a specially constructed quartz stirred cell (Hellma, Jena), which can easily be mixed thoroughly during the measurement by a magnetic stirrer bar (Teflon-coated, 8×3 mm, Hellma, Jena) stirring on the circular base of the cell, was used. The appropriate stirred cell holder with associated magnetic stirrer (Kontron, Neufahrn) of variable adjustable speed was furthermore used. A sample of the dressing cotton (approx. 10 mg) with immobilized SOD was placed over the magnetic stirrer bar. An equally heavy untreated medicinal cotton piece served as a control in the reference position. The cotton gauzes were separated from the liquid lying on top by a specially constructed insert, so that floating of any fluff which became detached was prevented, but exchange of all the reaction participants by mixing was still ensured. The beam was not blocked by incorporation of the insert. The reaction was started by addition of BXT-01050. Adjustment of the amount of enzyme to the minimum and maximum auto-oxidation rates required was achieved through the weight of sample to be added. The activity of the immobilized enzyme was calculated according to the manufacturer's formula (see above). The result was calculated in U-525 units per mg sample weight and standardized to 1 g sample weight. Each sample was subjected to at least a 5-fold determination.

Catalase Immobilized on Cellulose

The activity was determined in principle by the method already described for dissolved catalase (see above). The adaptation of the apparatus of the measurement system required for the determinations of the activity of immobilized enzymes has already been described above (for SOD).

The reaction was started by addition of the hydrogen peroxide-containing buffer. The amount of enzyme was adjusted to the required limit values through the weight of sample added. The activity of the immobilized enzyme was calculated by the following equation:

Activity [U] per sample weight=(17×13)/time recorded [s]·sample weight [mg]

The result was extrapolated for 1 g of sample. Each sample was subjected to at least a 5-fold determination.

Anti-PDGF Antibody Immobilized on Cellulose

The activity of the anti-PDGF antibody immobilized on dressing cotton was determined by bonding of PDGF—AB heterodimer. For this, samples of dressing cotton of 10 to 250 mg were incubated with PDGF—AB (50 ng/ml) in physiological sodium chloride solution for 30 min at room temperature. Thereafter, the samples were rinsed several times, and the concentration of PDGF—AB which remained was determined by the ELISA described in PCT/EP93/02295 (column 12, lines 27–32).

Trypsin Inhibitor Immobilized on Cellulose

The activity of the coupled trypsin inhibitor was determined via its ability to inhibit the activity of trypsin. The trypsin activity was determined in principle by the method of G. W. Schwert and Y. Takenaka (Biochim. Biophys. Acta 1955; 16:570–575). In this method, N-benzoyl-L-arginine is liberated from the substrate N-benzoyl-L-arginine ethyl ester (BAEE) by the trypsin activity.

The increase in extinction at 253 nm resulting by this reaction was monitored in present case with a spectrophotometer (Uvikon 943, Kontron, Neufahrn).

Cellulose pieces of various weights (10–50 mg) coupled with trypsin inhibitor were weighed and placed in 2.8 or 5.6 ml of the substrate solution. The substrate solution was prepared as described in "Bestimmungsmethoden für Enzyme [Determination methods for enzymes]" (B. Stellmach, Steinkopff Verlag Darmstadt, 1988, p. 266). The mixture was temperature-controlled at 25° C. and shaken (GFL water-bath 1083, GFL, Großburgwedel), and the reaction was started by addition of 0.2 ml or 0.4 ml of a trypsin solution (approx. 150 units/ml, dissolved in 0.001 N HCl). 0.5 ml of the supernatant was then transferred into a fresh quartz cell once a minute for at least 5 minutes and the extinction was determined at 253 nm. The cell contents were returned to the reaction mixture as quickly as possible. When the increase in the extinction per minute was constant, the measurement was ended and the trypsin activity was calculated according to the calculation formula in the stated publication by B. Stellmach:

$$\frac{E_{253}}{0.001 \cdot E_w} = \text{units/mg}$$

$E_{253}$: increase in extinction at 253 nm/min 0.001: 1 unit denotes an increase in extinction of 0.001/min $E_w$: weight of trypsin in mg/0.2 ml (or 0.4 ml) of solution employed.

Cellulose samples without pre-treatment and samples without activation but with inhibitor treatment served as controls. The results of the controls were taken into account when calculating the activity of the immobilized inhibitor. By plotting a standard straight line with dissolved trypsin inhibitor, it was possible to estimate the amount of immobilized inhibitor.

What is claimed is:

1. A method of healing a wound comprising applying to a wound a composition comprising a carrier covalently bonded to at least one substance which interacts with interfering factors present in a wound exudate, said wound healing process being impeded by said factors, the interfering factors being ions and the substance which interacts with the interfering factors is a chelator.

2. A method according to claim 1, wherein the chelator is selected from the group consisting of deferrioxamine, diethylenetriaminepentaacetic acid, N,N'-bis-(o-hydroxybenzyl)-ethylenediamine-N,N'-diacetic acid, 1,2-dimethyl-3-hydroxy-pyrid-4-one and 1,2-dimethyl-3-hydroxyl-3-hydroxypyridin-4-one.

3. A method according to claim 2, wherein the interfering factors are iron(III) ions and the substance which interacts with the interfering factors is deferrioxamine.

4. A wound covering comprising a carrier covalently bound to at least one substance which interacts with interfering factors present in a wound exudate, which factors impede wound healing and are ions, said substance being a chelator selected from the group consisting of deferrioxamine, diethylenetriaminepentaacetic acid, N,N'-bis-(o-hydroxybenzyl)-ethylenediamine-N,N'-diacetic acid, 1,2-dimethyl-3-hydroxy-pyrid-4-one and 1,2-dimethyl-3-hydroxyl-3-hydroxypyridin-4-one.

5. A wound covering according to claim 4, wherein the interfering factors are iron(III) ions and the substance which interacts with the interfering factors is deferrioxamine.

6. A method of healing a wound comprising applying to a wound a composition comprising a carrier covalently bonded to at least one substance which interacts with interfering factors present in a wound exudate, said wound healing process being impeded by said factors, the interfering factors being selected from the group consisting of antigens, free radicals, ions, proteins, peptides, lipids and free fatty acids, said substance bonding, complexing or chelating said factors or chemically reacting with said factors.

7. A wound covering comprising a carrier covalently bound to at least one substance which interacts with interfering factors present in a wound exudate, which factors impede wound healing and are selected from the group consisting of antigens, free radicals, ions, proteins, peptides, lipids and free fatty acids, said substance bonding, complexing or chelating said factors or chemically reacting with said factors.

* * * * *